United States Patent [19]

Inoue et al.

[11] 4,005,398
[45] Jan. 25, 1977

[54] METHOD OF DETERMINING THE DRIVER'S SUFFICIENT ALERTNESS TO DRIVE A MOTOR VEHICLE SAFELY

[75] Inventors: Naohiko Inoue; Takayuki Yanagishima, both of Yokohama; Hiromichi Nakamura, Yokohama; Noburu Fukasawa, Kamakura, all of Japan

[73] Assignee: Nissan Motor Co., Ltd., Japan

[22] Filed: Mar. 19, 1975

[21] Appl. No.: 559,922

[30] Foreign Application Priority Data

Apr. 16, 1974 Japan .............................. 49-41749

[52] U.S. Cl. .................................. 340/279; 180/99
[51] Int. Cl.² ......................................... G08B 21/00
[58] Field of Search ...................... 340/279; 180/99

[56] References Cited

UNITED STATES PATENTS

| | | | |
|---|---|---|---|
| 3,186,508 | 6/1965 | Lamont | 340/279 |
| 3,222,639 | 12/1965 | Kayser, Jr. | 340/279 |
| 3,611,344 | 10/1971 | Couper | 340/279 |
| 3,654,599 | 4/1972 | Sepper | 340/279 |
| 3,811,116 | 5/1974 | Takeuchi et al. | 340/279 |
| 3,877,541 | 4/1975 | Takeuchi et al. | 340/279 |

*Primary Examiner*—Glen R. Swann, III
*Attorney, Agent, or Firm*—Robert E. Burns; Emmanuel J. Lobato; Bruce L. Adams

[57] ABSTRACT

A constant voltage developed by a constant voltage generator is integrated, and the integrated voltage is applied to a voltage comparator. A standard voltage is applied to a voltage controller, which includes a sensor responsive to vehicle operating conditions, to control the level of the standard voltage to indicate the degree of driver alertness necessitated by the vehicle operating conditions. The controlled standard voltage is also applied to the voltage comparator, and when the integrated voltage exceeds the controlled standard voltage the comparator develops a warning signal output. A warning device receives the warning signal and is thereby rendered operative in order to alert the driver.

3 Claims, 3 Drawing Figures

METHOD OF DETERMINING THE DRIVER'S SUFFICIENT ALERTNESS TO DRIVE A MOTOR VEHICLE SAFELY

BACKGROUND OF THE INVENTION

This invention relates generally to a method of assuring safe driving, and particularly to a method of detecting a vehicle driver's alertness to drive safely and to alarm the driver when his alertness falls below a preselected level.

Heretofore, several methods have been proposed for preventing dangerous driving due to a driver's low alertness resulting from, for example, overfatigue, dozing or intoxication by drugs such as alcohol. One conventional method is to require the vehicle driver to respond to external stimuli in order to check the degree of his alertness. Another one is carried out by examining the driver's physical condition by, for example, observing the driver's eyeball movement which is sensed by a suitable sensing means attached to the driver's head.

However, several defects are encountered in the above-mentioned prior art as discussed below. That is, these methods are not practically suitable in that the detection of the driver's low alertness is comparatively slow and often erroneous, and furthermore it is very cumbersome to the driver to drive with the eyeball movement sensing means.

SUMMARY OF THE INVENTION

According to the invention, a falling off of a vehicle driver's alertness below a predetermined level is determined when the frequency of the driver's manipulation of the vehicle falls below a preselected value for a preselected time level. More specifically, the method according to the invention comprises: generating a signal having a preselected constant voltage, integrating the signal with respect to time, generating a standard voltage indicating a minimum allowable limit of the driver's alertness required for safe driving in usual driving circumstances, comparing the magnitudes of the above two kinds of voltages, warning the driver when the first-mentioned voltage exceeds the standard voltage, and sensing the driver's alertness sufficient for the safe driving and then immediately resetting the integrating and also stopping the warning.

An object of the invention is to present an improved method of detecting a vehicle driver's alertness and warning him when his alertness falls below a preselected level.

BRIEF DESCRIPTION OF THE DRAWING:

Additional objects as well as features and advantages of the invention will become evident from the detailed description set forth hereinafter when considered in conjunction with the accompanying drawings, wherein like parts in each of the several figures are identified by the same reference numerals, and wherein.

DESCRIPTION OF THE PREFERRED EMBODIMENT

Figure 1:
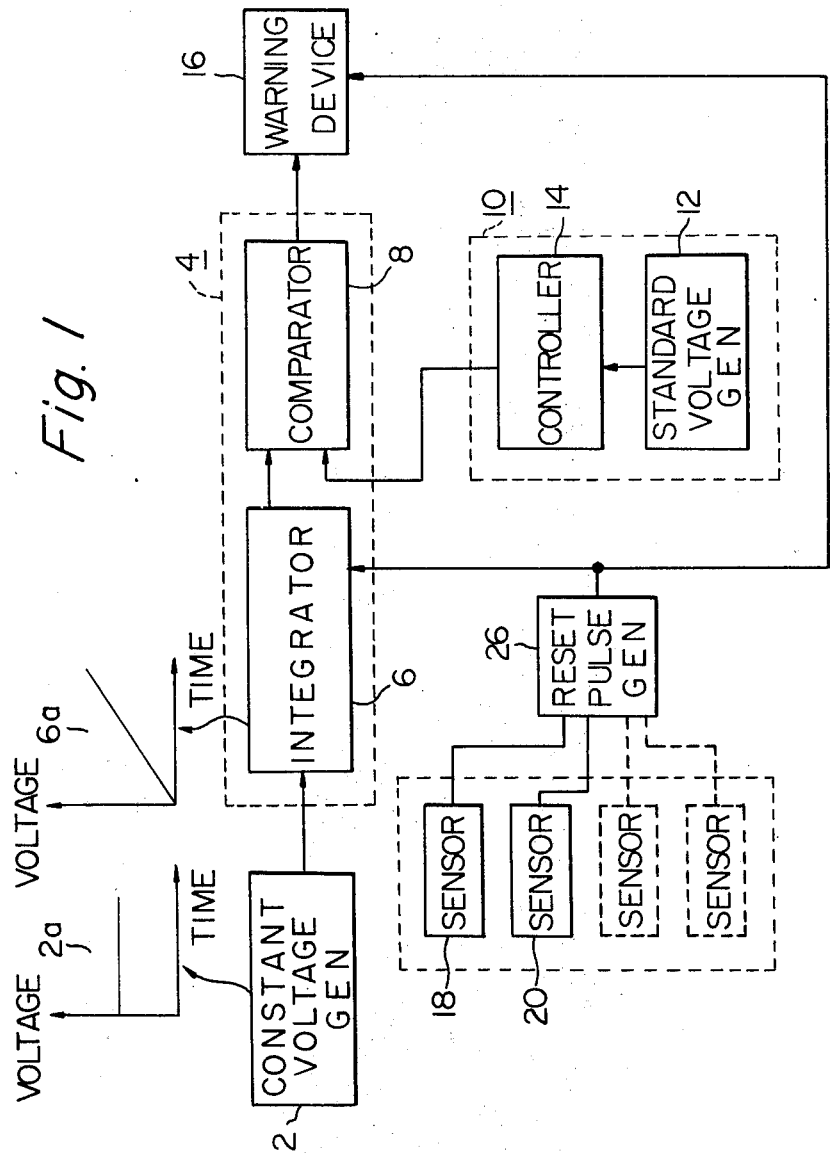
FIG. 1 is a block diagram illustrating a method according to the invention.

Reference is now made to the accompanying drawings, especially to FIG. 1, wherein a preferred embodiment of the invention is schematically depicted. The FIG. 1 embodiment circuit is designed to detect a falling off of a vehicle driver's alertness below a predetermined level to alert the driver that he is incompetent for safe driving. In general, according to the invention, a falling of the driver's consciousness below the predetermined level is determined when, for example, the frequency of driving manipulation by the driver falls below a preselected value for a preselected time interval. In FIG. 1, when the driver switches on a starting switch (not shown) such as an ignition switch, a constant voltage generating unit 2 starts to feed a preselected constant voltage, as shown in a graph 2a, into a discriminating section 4 comprising an integrator 6 and a comparator 8. The integrator 6 integrates the constant voltage with respect to time. Thus the output of the integrator 6 linearly continuously increases with the lapse of time as viewed in a graph 6a. The comparator 8 receives two kinds of electrical signals, one of which is the integrated voltage fed from the integrator 6, and the other is a standard voltage applied from a standard voltage generating section 10 and representing an allowable minimum limit of the driver's alertness for safe driving in usual driving circumstances. As shown, the section 10 comprises a standard voltage generator 12 and a standard voltage controller 14. The controller 14 controls the standard voltage in accordance with changing driving conditions such that the standard voltage is lowered as the driver's alertness is more required such as during high speed driving. The comparator 8, to which the aforementioned two kinds of signals are applied, compares the magnitudes of these signals. If the signal from the integrator 6 exceeds that from the section 10, the comparator 8 energizes a suitable device 16 such as a buzzer or a light for warning the driver that he is incompetent for safe driving. In the above, it is understood that when the driver's alertness is required more than usual for safe driving, the warning is carried out more quickly than under usual driving conditions, because the standard potential from the generator 12 is lowered in such a condition as previously discussed.

As shown, a sensor 18 is provided to sense the driver's alertness sufficient for safe driving to apply its output to a reset signal generator 26. The generator 26 is an OR gate circuit and develops on its output terminal a reset signal when receiving the output signal from the sensor 18. For use as the sensor 18, the alarm apparatus for vehicle operator disclosed in U.S. Pat. No. 3,222,639 is suitable. The reset signal from the reset signal generator 26, which is fed to both the integrator 6 and the warning device 16, clears or resets the integrating operation of the integrator 6; in other words, causes the integrator 6 to start again its operation from the beginning, and on the other hand, stops the warning signal if the warning device 16 is in operation. In the present embodiment, the provision of the single sensor, viz., 18 is sufficient for the purpose of the present invention. However, although not disclosed in detail in the specification, another sensor 20 is also shown, and includes circuitry to count the frequency of the driver's manipulation of instrument light switches such as a turning direction signal switch and a radio switch to generate a signal when the frequency for a preselected time interval exceeds a preselected value.

Additionally, still another sensor can be used to count the frequency of the driver's manipulation of the clutch and the brake to generate a signal when the frequency for a preselected time interval exceeds a preselected value.

Figure 2:
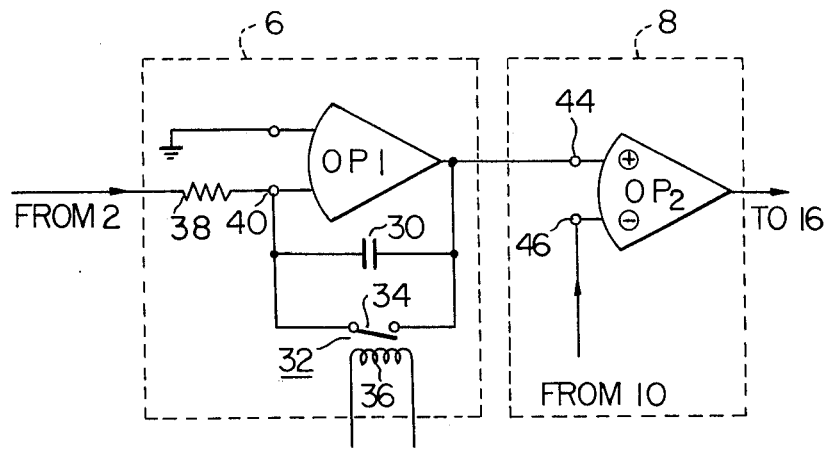
FIG. 2 shows a preferred embodiment of a part of FIG. 1.

In FIG. 2, there is illustrated an embodiment of the discriminating section 4, wherein two operational amplifier OP1 and OP2 correspond to the integrator 6 and the comparator 8, respectively. To an input terminal of the OP1 is connected the constant voltage generator 2 (not shown in FIG. 2) through a suitable resistor 38, and the other input terminal thereof is grounded. A capacitor 30 is inserted in a feedback path of the OP1 for the purpose of integration. Across the capacitor 30 connected is a relay 32 in such a manner that its contact 34 is connected across the capacitor 30 and its coil 36 to the reset signal generator 26 (not shown in FIG. 2). Thus, when the reset signal is applied to the relay coil 36, the contact 34 is closed due to energization of the coil 36 to short-circuit the capacitor 30, resulting in resetting of the OP1 because of discharge of the capacitor 30. As shown, the output terminal of the OP1 is connected to one of the input terminals of the OP2. The other input terminal of the OP2 is coupled to the standard voltage generating section 10 for receiving the standard voltage. The OP2 compares the two kinds of signals as previously discussed and the output terminal thereof is connected to the warning device 16 (not shown in FIG. 2). In the above, detailed functions of the OP1 and OP2 are not mentioned since they are familiar to those skilled in the art.

Figure 3:
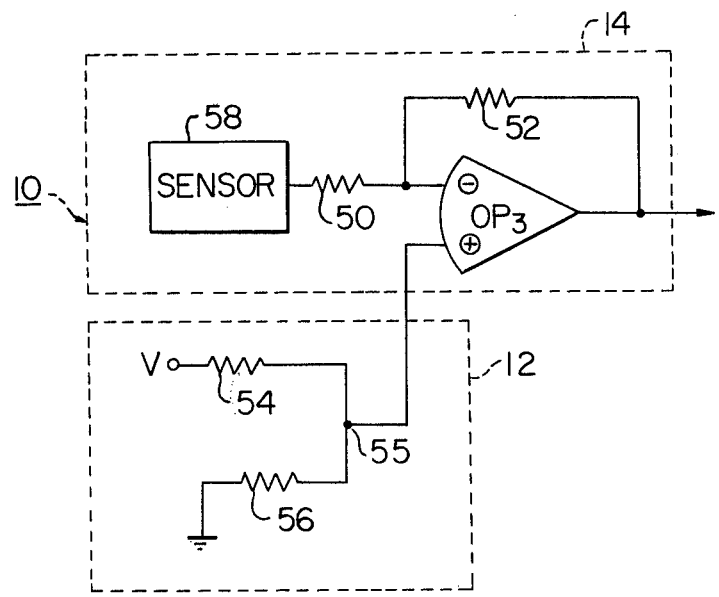
FIG. 3 shows a preferred embodiment of another part of FIG. 1.

Reference is made to FIG. 3, wherein there is illustrated an embodiment of the standard voltage generating section 10. Two resistors 54 and 56 are connected in series with each other and interposed between a constant d.c. power source such as a car battery and ground for generating the standard voltage on a junction 55. The junction 55 is connected to one of the input terminals of an operational amplifier OP3 of the controller 14. To the other input terminal of the OP3 connected is a sensor 58 over a suitable resistor 50. The OP3 has a resistor 52 in its feedback path and is arranged to find the difference of the potential between the two signals from the sensor 58 and the junction 55.

In the foregoing description, the constant voltage generator 2 of FIG. 1 can be modified to produce a voltage which is changed in response to a vehicle speed. This means that a failure in the driver's alertness below the predetermined level is checked when the frequency of the driver's driving manipulation falls below a preselected value for a preselected travelling distance in place of a preselected time interval as previously mentioned. In this case, it is understood that the higher the vehicle speed, the higher the integrated voltage appearing at the output terminal of the integrator 6 is, so that the warning is carried out more quickly than at low vehicle speed. This is therefore very advantageous for avoiding traffic accidents due to high speed driving. Furthermore, in connection with FIG. 1 the warning device 16 has been stated to stop its operation by the reset signal from the reset signal generator 26, however, the stoppage can be also carried out in different manners. That is, the warning device 16 may be automatically de-energized after a preselected time interval by means of a timer, for example. Another method is to stop the warning of the device 16 only when the driver switches off the ignition switch of the vehicle.

From the foregoing description, it will be understood that the method according to the invention is quite simple and quite useful to avoid traffic accidents due to failure of a driver's alertness.

What is claimed is:
1. A method of determining driver's alertness and warning the driver when his alertness falls below a preselected level while driving a vehicle, which comprises the steps of:
    generating a first signal having a preselected constant potential;
    integrating the first signal with respect to time;
    generating a second signal which is a standard potential indicative of a minimum allowable limit of the driver's degree of alertness;
    comparing the magnitudes of the integrated first and the second signals;
    warning the driver when the magnitude of the integrated first signal exceeds that of the second signal; and
    sensing the driver's sufficient alertness for safe driving to reset the integrating and to stop the warning.
2. A method as claimed in claim 1, further comprising the step of:
    stopping automatically the warning after a lapse of a preselected time interval.
3. A method as claimed in claim 1, further comprising the step of:
    stopping the warning only when the driver switches off the ignition switch of the vehicle.

* * * * *